United States Patent [19]
DeLago

[11] Patent Number: 5,827,227
[45] Date of Patent: Oct. 27, 1998

[54] CATHETER HAVING A RADIALLY ADJUSTABLE SHEATH

[76] Inventor: Augustin J. DeLago, 11 Pheasant La., Menands, N.Y. 12202

[21] Appl. No.: 682,326

[22] Filed: Jul. 17, 1996

[51] Int. Cl.⁶ .................................................. A61M 29/00
[52] U.S. Cl. ........................... 604/104; 604/171; 604/167
[58] Field of Search .................................... 604/167, 166, 604/171, 158, 104

[56] References Cited

U.S. PATENT DOCUMENTS

| | | | |
|---|---|---|---|
| 3,789,852 | 2/1974 | Kim | 604/104 |
| 4,000,739 | 1/1977 | Stevens | 604/167 |
| 5,127,627 | 7/1992 | Wiser . | |
| 5,201,756 | 4/1993 | Horzewski et al. . | |
| 5,221,264 | 6/1993 | Wilk | 604/167 |
| 5,256,150 | 10/1993 | Quiachon | 604/171 |
| 5,312,360 | 5/1994 | Behl . | |
| 5,318,588 | 6/1994 | Horzewski et al. . | |
| 5,330,437 | 7/1994 | Durman | 604/167 |
| 5,397,335 | 3/1995 | Gresl | 604/167 |
| 5,411,483 | 5/1995 | Loomas et al. . | |

*Primary Examiner*—Sam Rimell
*Assistant Examiner*—Luke J. Yeh
*Attorney, Agent, or Firm*—Schmeiser, Olsen & Watts

[57] ABSTRACT

A radially adjustable catheter apparatus and valve therefor is disclosed. The catheter apparatus used to provide percutaneous access to inner body cavities. The catheter apparatus is includes a tubular sheath, a tubular dilator extending through and beyond the sheath member and a flexible guide wire extending through the dilator. The sheath and dilator each extend from hollow housings, which interlock and fixedly retain the dilator within the sheath. The sheath further includes at least one pleat or fold along its longitudinal axis for expanding the diameter of the sheath. Disposed within the sheath housing are a hemostatic valve and a diaphragm, which effectuate hemostatic seals around the dilator and sheath, respectively. In a preferred embodiment, there is a pair of slidable plates, each having a semicircular aperture equal in diameter to the open end of the pleated sheath, affixed to the open end of the sheath member which is within the housing. The slidable plates move radially outward as the diameter of the sheath is expanded, thus allowing dilator of increasing diameter to be inserted therethrough.

14 Claims, 3 Drawing Sheets

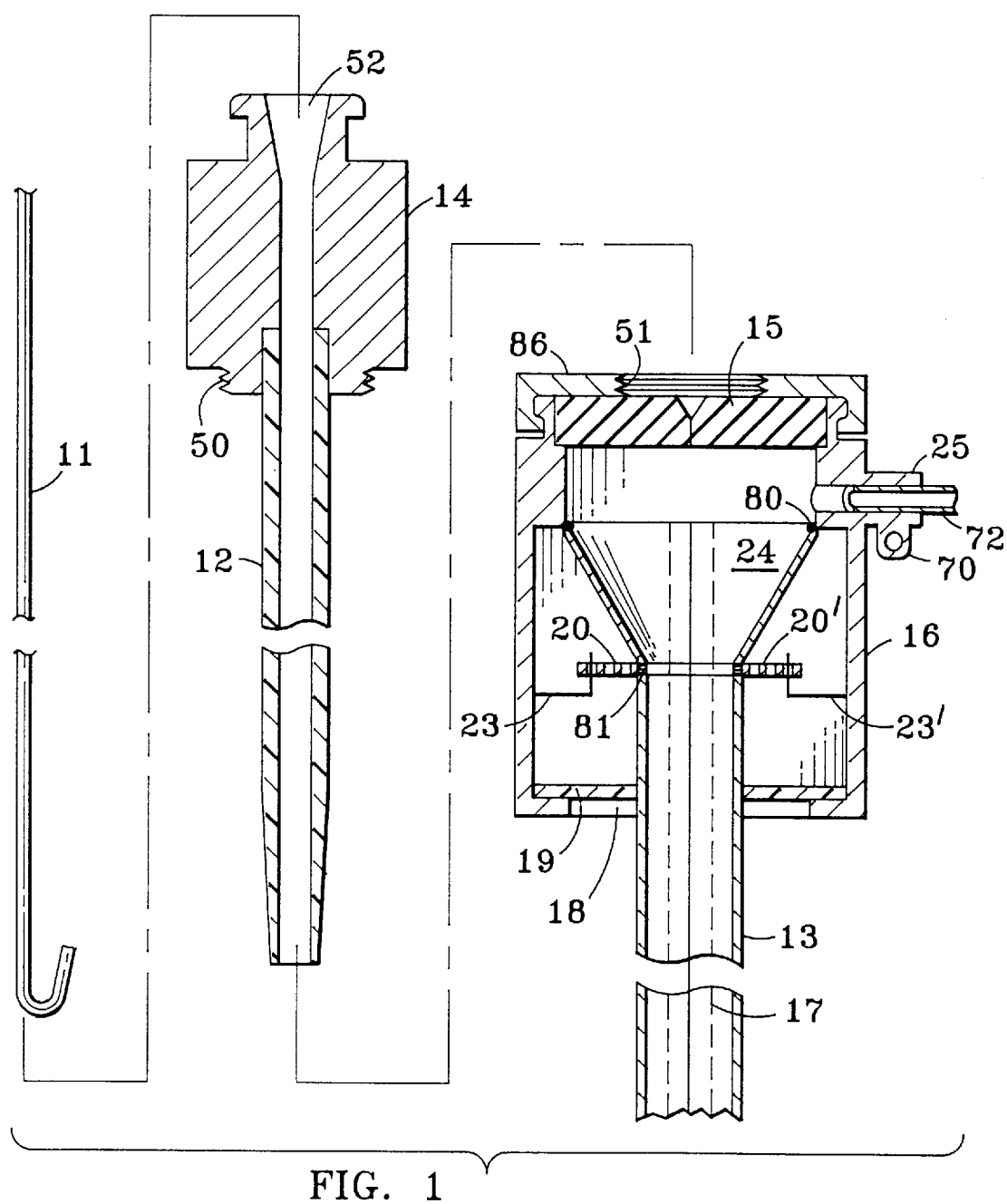
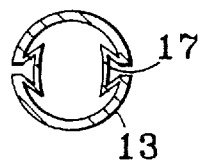
FIG. 1
FIG. 2

CATHETER HAVING A RADIALLY ADJUSTABLE SHEATH

TECHNICAL FIELD

This invention relates generally to apparatus for providing percutaneous access to the interior of body cavities. More particularly, this invention relates to the construction of a catheter assembly for introducing dilators of various dimensions into a hollow body cavity.

BACKGROUND OF THE INVENTION

For various reasons, it is often necessary to obtain percutaneous access to a hollow body cavity of a patient. For example, it may be necessary to administer medication or to perform a diagnostic or interventional procedure within the cavity. Accordingly, various apparatus and methods have been developed to provide the necessary access to body cavities.

One common apparatus developed is a percutaneous catheter and dilator or opterator assembly. The assembly typically comprises a hollow tubular catheter sheath, having a hollow, open-ended housing at one end, and a hollow, tubular dilator or opterator, having a tapered end and a hollow open-ended housing at an opposite end. Located within the housing of the sheath, distal from the sheath, is a valve which functions to effectively seal the open end of the housing. To assemble the apparatus, a guide wire is inserted through the dilator housing and into the dilator tube. The tapered end of the dilator is then inserted into the sheath housing, through the valve and out through the open distal end of the sheath. The housings of the dilator and sheath are constructed such that they are releasably engagable, for instance by a snap-fit or complementary threaded portions. The guide wire includes an anchor means on the end within the catheter, such as a flexible "J" or "T"-shape. The sheath housing can also include a side-arm assembly which provides a means for administering medications or other fluids.

Once assembled, the catheter assembly can then be percutaneously inserted into a body cavity. To insert the assembly, the dilator tip is inserted, generally through a small puncture hole, until the sheath housing abuts the puncture site. After the assembly is properly positioned within the body cavity, the hook end of the guide wire is pushed out through the dilator, into the cavity, where it becomes anchored. Typically, the sheath housing will also include means, such as a tie-down tab to accommodate a stitch, for securing the housing to the patient's skin.

Generally, catheter assemblies are available in varying tubular diameters or "French sizes", the choice of which is determined by the procedure to be accomplished. For example, the performance of an angiogram would require the use of a 6–7 French catheter sheath while a angioplasty would require the use of an 8–9 French catheter sheath. Often, it is desired to perform two different procedures, one after the other, wherein each procedure requires a different French size. In this instance, both the dilator and catheter must be withdrawn, leaving the guide wire intact, and a larger assembly then reinserted, over the guide wire. This procedure has several disadvantages, most notably of which is the irritation and damage that is done to body tissue by withdrawing and reinserting the assembly. Also important is the threat of backflow of blood, potential blood loss and the increased chance of infection as the entry site is left open and exposed prior to the reinsertion of the replacement assembly. Moreover, when the assembly is being utilized to administer medications or fluids, their administration must be interrupted during the positioning of the new assembly.

It is therefore desirable to provide a catheter apparatus wherein the catheter sheath is expandable and capable of accommodating dilators of increasing diameters thereby eliminating the need to remove and replace the entire assembly if a larger catheter or dilator is needed. Furthermore, such a catheter apparatus needs to be expandable while still maintaining the integrity of a sealed unit to prevent the backflow of blood during the removal and replacement of the dilator.

U.S. Pat. Nos. 5,201,756 and 5,318,588, issued Apr. 13, 1993 and Jun. 7, 1994, respectively, to Horzewski et al. and assigned to Danforth Biomedical, Inc., disclose a radially expandable intravascular device which is comprised of a plurality of members. The first member is an outer tube-shaped sheath which is radially expandable by being formed of an elastic-type material. The second member is an inner portion extending throughout the outer tube. The inner portion includes a slit such that it is also radially expandable. The device can be inserted into a body cavity and diagnostic or therapeutic objects or the like can be conveyed through the device while still enabling the device to have a smaller cross-section throughout most of its length than the object conveyed therethrough. The apparatus includes an adjustable O-ring valve disposed within the lumen of an adaptor (housing) and allows the distal aspect of the shaft lumen to be sealed and thus preclude the loss of blood during the introduction and withdrawal of devices of various diameter. The O-ring can be compressed and released by rotating two components of the adaptor (housing).

U.S. Pat. No. 5,312,360, issued May 17, 1994 to Behl and assigned to Innerdyne Medical, Inc., teaches a dilator assembly which uses a plurality of dilation members which are generally similar in construction, but which have successively larger cross-sectional areas so that the size of the percutaneous penetration can be increased by introducing successively larger dilators over the guide member.

U.S. Pat. No. 5,221,264, issued Jun. 22, 1993 to Wilk et al., discloses a reduction port for a trocar sleeve which comprises a plate having an aperture of a predetermined diameter and a pair of doors slidably mounted to the plate for reducing the size of the aperture. Each door is provided with a semicircular aperture having a diameter equal to the reduced diameter of the aperture. The sliding doors reduces the size of the aperture from the predetermined diameter of the plate aperture to the smaller predetermined diameter of the doors' aperture.

U.S. Pat. No. 5,411,483, issued May 2, 1995 to Loomas et al., discloses a seal for use in a surgical instrument to provide a gas-tight seal with an instrument passed through the seal. The seal accommodates instruments of various diameters. The seal comprises a seal body, an instrument seal and a laterally-compliant seal mounting. The instrument seal is made of an elastic material and includes an instrument port formed therein. A hardened plastic seal mounting mounts the instrument seal to the seal body and forms a gas-tight seal between the instrument seal and the seal body.

SUMMARY OF THE INVENTION

An expandable, self-sealing catheter apparatus is disclosed. The apparatus comprises an expandable catheter sheath, a tapered end dilator and a guide wire. The guide wire is inserted into the dilator which is inserted within the catheter sheath. The dilator and the sheath each include a housing which is engagable with the other. The housing of the sheath further includes a valve and a diaphragm which combine to form a hemostatic seal around the dilator.

It is an advantage of the present invention to provide an expandable catheter sheath that is capable of accommodating dilators of various diameters.

It is an advantage of the present invention to provide a catheter sheath which is of simple construction.

It is an advantage of the present invention to provide a catheter having a guide for a sheath, wherein the guide may be radially adjustable or radially flexible.

It is a further advantage of the present invention to provide a valve seal for the housing of the catheter sheath which is capable of accommodating dilators of various diameters while still maintaining an integral seal over the open pathway to the interior of a body cavity.

BRIEF DESCRIPTION OF THE DRAWINGS

Numerous other advantages and features of the present invention will become readily apparent from the following detailed description of the preferred embodiment, the appended claims and the accompanying figures, wherein like reference numerals refer to like features throughout and wherein:

FIG. 1 is a cross sectional view of one embodiment of the catheter assembly of the present invention;

FIG. 2 is a cross sectional view, taken along line 2—2 of FIG. 1, of the sheath member, showing the expandable pleats;

DETAILED DESCRIPTION OF THE PREFERRED EMBODIMENT

Figure 3A:
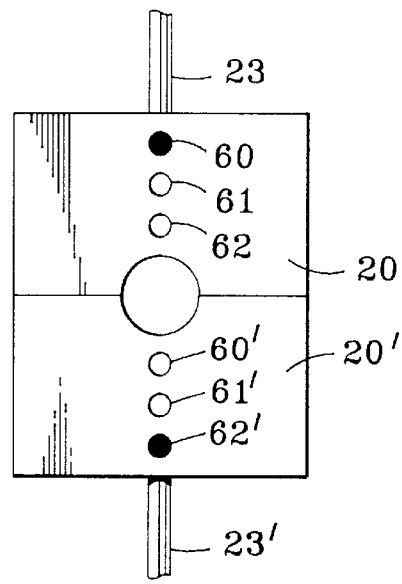
FIG. 3A is a front view of the slidable plates of one embodiment of the catheter assembly of the present invention, shown in a first position.

Although this invention is susceptible to embodiment in many different forms, preferred embodiments of the invention are shown. It should be understood however, that the present disclosure is to be considered as an exemplification of the principles of this invention and is not intended to limit the invention to the embodiments illustrated.

Referring now specifically to the drawings, there is shown a catheter apparatus, generally designated as 10, 110 for percutaneous access to a body cavity and which is basically comprised of three components: a guide wire 11, 111 a dilator 12, 112 and a sheath 13, 113. When assembled, guide wire 11, 111 extends through dilator 12, 112 which in turn, extends through and beyond, sheath 13, 113. To use catheter apparatus 10, 110 the tip of dilator 12, 112 which extends beyond sheath 13, 113 is inserted into a body cavity, generally through a small puncture hole, whereby dilator 12, 112 is then pushed over the guide wire 11, 111 where it becomes anchored within the cavity. Guide wire 11, 111 can then serve as a guide for subsequent withdrawals and insertions of medical instruments or medications into the body cavity. Guide wire 11, 111 is made from a basically flexible material and generally will include a flexible J or T-shaped end that is capable of being anchored within a body cavity.

Dilator 12, 112 is a hollow, open-ended tubular member, having a tapered end, made from a flexible, relatively elastic material, such that it can flex without becoming kinked or bent as it is inserted into the body. At an end of dilator 12, 112 opposite from the tapered end, is a hollow, open-ended housing 14, 114 which is used to securely engage dilator 12, 112 within sheath 13, 113 by threads 50, 51. Housing 14, 114 includes an insertion port 52 to guide the guide wire 11,111 into dilator 12, 112.

Sheath 13, 113 is a hollow, open-ended tubular member which is secured within and extends from a hollow, open-ended housing 16, 116. Valve 15, 115 is held in the housing 16, 116 by cap 86. Sheath 13, 113 is formed from a flexible, relatively elastic material, which may or may not be transparent. As shown in FIG. 2, sheath 13 is formed such that it includes at least one pleat 17 in its longitudinal axis (two are shown), which function to expand the diameter of sheath 13 when they are opened. As one skilled in the art will recognize, it is not necessary that pleat 17 be formed in the manner shown, and other methods of pleating or folding sheath 13 can be envisioned.

Figure 3B:
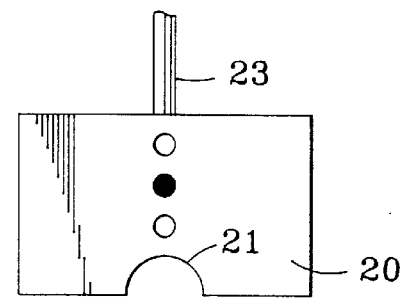
FIG. 3B is a front view of the slidable plates of one embodiment of the catheter assembly of the present invention, shown in a second position.
Figure 3C:
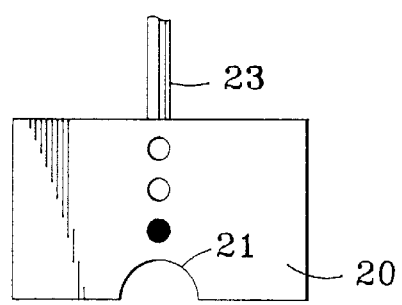
FIG. 3C is a front view of the slidable plates of one embodiment of the catheter assembly of the present invention, shown in a third position.
Figure 3C:
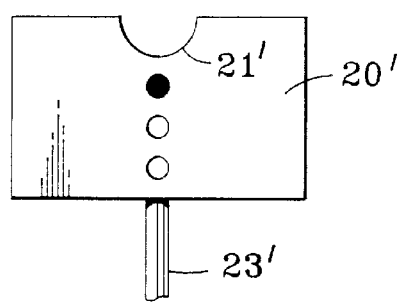

In one embodiment of catheter apparatus 10, as shown in FIG. 1, sheath 13 enters housing 16 through opening 18, where it then passes through diaphragm 19. Diaphragm 19 is formed of a highly elastic material, ensuring a hemostatic seal around sheath 13. Mounted within housing 16 are two slidable plates, 20 and 20'. As shown in FIGS. 3A, 3B and 3C, plates 20 and 20' are provided with a semicircular aperture, 21 and 21', which are equivalent in diameter to the diameter of pleated sheath 13, which is attached to and passes therethrough. Plates 20 and 20' also include a plurality of apertures 60, 61, 62 and 60', 61', 62', in substantially vertical alignment and in substantially parallel alignment with the longitudinal axis of sheath 13. Preferably, plates 20 and 20' include at least three sequential apertures 60, 61, 62, and 60', 61', 62', such that sheath 13 can be expanded to at least three increasing French sizes. Plates 20 and 20' are mounted within housing 16 by clips 23 and 23' which extend from opposing sides of the inner surface of housing 16. Extending from the face of plates 20 and 20' to the inner surface of housing 16 is a funnel-shaped guide 24, having flexible joints 80, 81 which function to guide dilator 12 into sheath 13. As seen in FIG. 1, the housing 16 includes a side-port 25, which includes an attachment means 70 for attachment to a patient. A tube 72 also extends therefrom for attachment to a stopcock (not shown). Tube 72 is used for insertion of medicines or other fluids into the body. Disposed above funnel-shaped guide 24 is a hemostatic valve 15 which is made from a highly elastic material and which includes an insertion port (not shown) for dilator 12. The hemostatic valve 15 is held in place by cap 86. Hemostatic valve 15 is self-sealing, expanding to accommodate dilator 12, and then immediately resealing when dilator 12 is withdrawn.

In practice, dilator 12 is inserted through the insertion port of hemostatic valve 15 and into sheath 13 through semicircular apertures 21 and 21'. When sheath 13 is in its pleated condition, clips 23 and 23' are engaged within the outermost of apertures 22 and 60', 61', 62'. As larger diameter dilators are inserted through hemostatic valve 15 and semicircular apertures 21 and 21', plates 20 and 20' move radially outward, and clips 23 and 23' become engaged within the appropriate one of apertures 60, 61, 62 and 60', 61', 62'. As plates 20 and 20' move to accommodate a larger dilator, pleats 17 expand, increasing and retaining the diameter of sheath 13.

Figure 4:
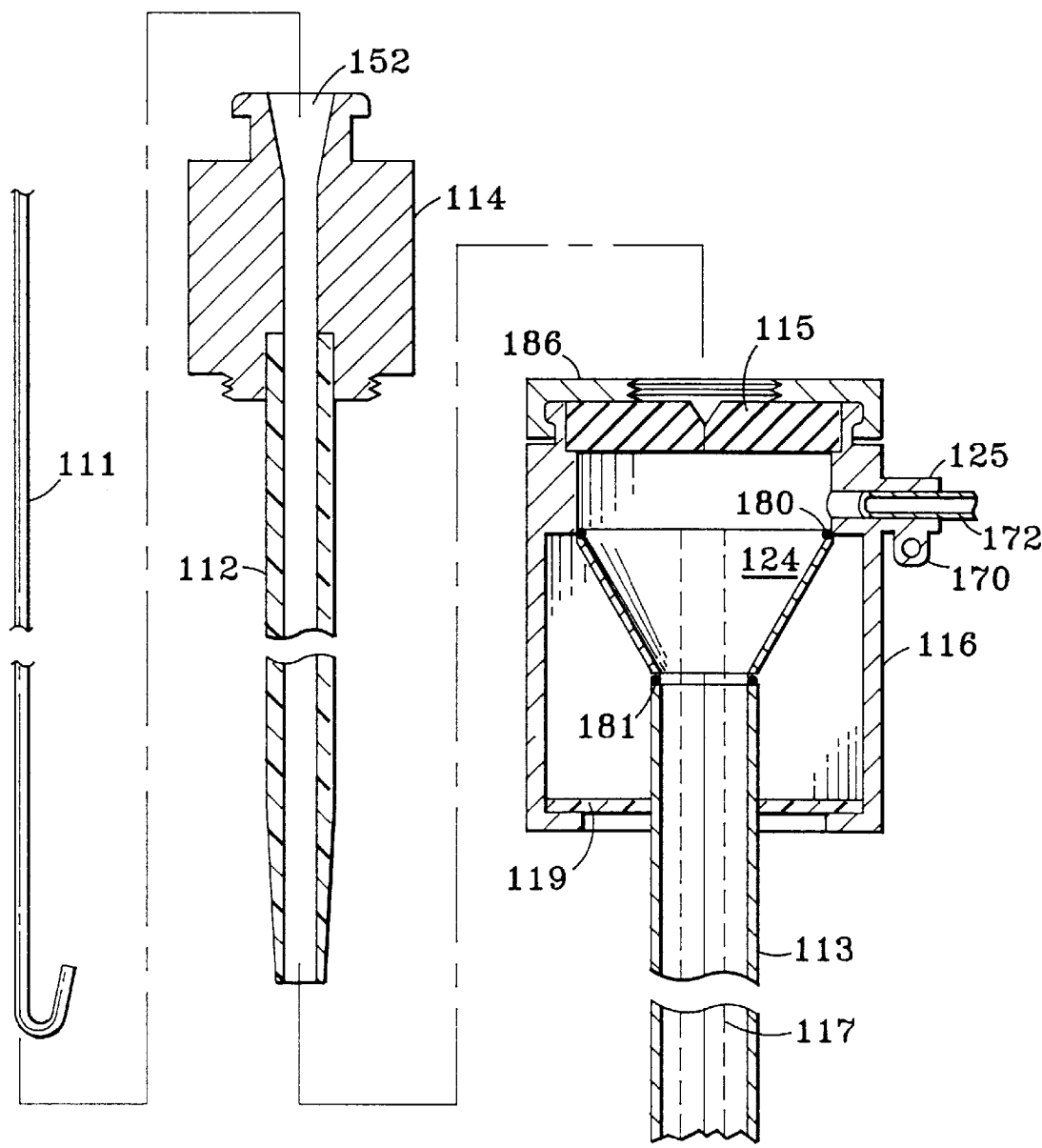
FIG. 4 is a cross sectional view of an alternate embodiment of the catheter assembly of the present invention.

Referring now to FIG. 4, in an alternate embodiment of the invention, the end portion of sheath 113, which is within housing 116, has a gradually increasing diameter, making it appear funnel-shaped 124. Disposed within funnel-shaped portion 124 is a hemostatic valve 115, formed of a highly elastic material and which includes an insertion port (not shown) for dilator 112. Hemostatic valve 115 is self-sealing, expanding to accommodate the diameter of dilator 112 and immediately resealing once dilator 112 is withdrawn. Funnel-shaped portion 124 of sheath 113 includes two flexible portions, 180 and 181, which are located at each of the vertices where the periphery of sheath 113 changes its planar orientation. Flexible portions 180 and 181 operate in conjunction with pleats 117 to expand the diameter of sheath 113.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

I claim:

1. A device, for percutaneous access to a patient, including a housing containing a hemostatic valve, said device comprising:

a radially adjustable sheath, operatively attached to said housing;

a flexible expandable funnel-shaped conduit operatively coupled to said radially adjustable sheath within said housing, said conduit being larger than said radially adjustable sheath; and an adjustment device, attached to said housing, for radially adjusting said sheath, wherein the adjustment device further comprises means for step-wise incremental adjustment of the sheath.

2. The device of claim 1, wherein said means for step-wise incremental adjustment comprises two plates having a plurality of holes and clips that may be inserted into said plates.

3. The device of claim 1, wherein said adjustment device further comprises a diaphragm.

4. The device of claim 1, wherein said sheath is pleated.

5. A catheter comprising:

a housing having a hemostatic valve;

a unitary radially adjustable sheath attached to said housing;

a dilator having a given diameter adapted for insertion through said hemostatic valve into said radially adjustable sheath, said radially adjustable sheath expanding to the given diameter; and means operatively coupled to said radially adjustable sheathe for holding said radially adjustable sheath at the given diameter upon removal of the dilator.

6. The device of claim 5 wherein said means for holding comprises two plates having a plurality of holes and clips that may be inserted into said plates.

7. The device of claim 1, wherein said means for holding further comprises a diaphragm.

8. The device of claim 1, wherein said means for holding further comprises a funnel operatively positioned between said sheath and said hemostatic valve.

9. The device of claim 8, wherein said funnel is radially adjustable.

10. The device of claim 5, wherein said sheath is pleated.

11. A device for percutaneous access to a patient said device comprising:

a housing;

a hemostatic valve operatively attached to said housing proximate to a first end of said housing;

a diaphragm attached to said housing proximate an end opposite said first end of said housing;

a radially adjustable sheath extending through said diaphragm;

an adjustment device, attached to said housing, for radially adjusting said sheath, wherein said adjustment device comprises an expandable funnel operatively coupled to said radially adjustable sheath in said housing; and a dilator having a given diameter adapted for insertion through said hemostatic valve into said radially adjustable sheath wherein insertion of said dilator into said radially adjustable sheath results in adjustment of a diameter of the radially adjustable sheath to correspond to the given diameter.

12. A method for radially adjusting a sheath on a catheter, said steps comprising:

providing a housing having a hemostatic valve operatively attached to said housing proximate a first end of said housing; a diaphragm attached to said housing proximate an end opposite said first end of said housing; and a radially expandable sheath therein and an adjustment device therefor;

selecting a dilator having a first diameter; and inserting said dilator into said sheath, thereby adjusting the diameter of the sheath to correspond to the first diameter.

13. The method of claim 12, further comprising the steps of:

selecting a dilator having a second diameter; and inserting said dilator into said sheath, thereby adjusting the diameter of the sheath to correspond to the second diameter.

14. An expandable catheter apparatus for use in providing percutaneous access to the interior body cavities of a patient, said expandable catheter apparatus comprising:

a housing having a first ad a second opening;

a diaphragm disposed within said housing proximate said second opening;

a hemostatic valve disposed within said housing proximate said first opening;

an elongate sheath extending from said second opening of said housing, wherein said sheath includes at least one pleat formed along its longitudinal axis;

an elongate dilator having a tapered first end and a second end;

an elongate guide wire, wherein said guide wire is inserted into said second end of said dilator and said tapered end of said dilator is inserted into said sheath through said first opening of said housing; and an adjustment device for radially adjusting said sheath, the adjustment device including a plurality of plates and a plurality of clips, wherein each of said plurality of plates includes at least two apertures through which the clips may be inserted to adjust the sheath.

* * * * *

UNITED STATES PATENT AND TRADEMARK OFFICE
CERTIFICATE OF CORRECTION

PATENT NO. : 5,827,227
DATED : Oct. 27, 1998
INVENTOR(S) : DeLago

It is certified that error appears in the above-identified patent and that said Letters Patent is hereby corrected as shown below:

Column 4, line 58, delete "22" and insert --60, 61, 62--.
Claim 5, Column 5, line 53, delete "sheathe" and insert --sheath,--.
Claim 14, Column 6, line 44, delete "ad" and insert --and--.

Signed and Sealed this

Ninth Day of March, 1999

Attest:

Q. TODD DICKINSON

Attesting Officer

Acting Commissioner of Patents and Trademarks